(12) United States Patent
Glenn et al.

(10) Patent No.: US 10,383,553 B1
(45) Date of Patent: Aug. 20, 2019

(54) DATA COLLECTION AND ANALYSIS FOR SELF-ADMINISTERED COGNITIVE TESTS CHARACTERIZING FINE MOTOR FUNCTIONS

(71) Applicant: The Cognitive Healthcare Company, San Francisco, CA (US)

(72) Inventors: Shenly Glenn, San Francisco, CA (US); Joel Mefford, Benicia, CA (US)

(*) Notice: Subject to any disclaimer, the term of this patent is extended or adjusted under 35 U.S.C. 154(b) by 373 days.

(21) Appl. No.: 14/883,450

(22) Filed: Oct. 14, 2015

Related U.S. Application Data

(60) Provisional application No. 62/063,939, filed on Oct. 14, 2014.

(51) Int. Cl.
  *A61B 5/16* (2006.01)
  *A61B 5/11* (2006.01)
  *G09B 5/02* (2006.01)
  *G16H 50/20* (2018.01)

(52) U.S. Cl.
  CPC .............. *A61B 5/1124* (2013.01); *A61B 5/16* (2013.01); *G09B 5/02* (2013.01); *G16H 50/20* (2018.01)

(58) Field of Classification Search
  None
  See application file for complete search history.

(56) References Cited

U.S. PATENT DOCUMENTS

| | | | |
|---|---|---|---|
| 5,956,671 A | 9/1999 | Ittycheriah et al. | |
| 8,606,581 B1 | 12/2013 | Quast et al. | |
| 8,781,831 B2 | 7/2014 | Ljolje et al. | |
| 8,830,189 B2 | 9/2014 | Rimon et al. | |
| 8,856,543 B2 | 10/2014 | Geiger et al. | |
| 8,866,752 B2 | 10/2014 | Westerman et al. | |
| 9,063,647 B2 | 6/2015 | Zotov et al. | |
| 9,075,462 B2 | 7/2015 | Sauer et al. | |
| 9,092,125 B2 | 7/2015 | Michaelis et al. | |
| 9,141,284 B2 | 9/2015 | Sands et al. | |
| 9,147,059 B2 | 9/2015 | Isbister et al. | |
| 2005/0080592 A1* | 4/2005 | Buscema ................. G09B 5/00 702/182 |
| 2006/0132283 A1 | 6/2006 | Eberhart et al. | |
| 2007/0298385 A1 | 12/2007 | Jenkins et al. | |
| 2011/0066082 A1 | 3/2011 | Duffy | |
| 2012/0030570 A1 | 2/2012 | Migos et al. | |
| 2012/0330178 A1* | 12/2012 | Kraft ..................... A61B 5/6898 600/544 |
| 2013/0216986 A1 | 8/2013 | Goldman et al. | |
| 2014/0026212 A1 | 10/2014 | Geiger et al. | |
| 2014/0336539 A1 | 11/2014 | Torres et al. | |
| 2015/0213244 A1 | 7/2015 | Lymberopoulos et al. | |
| 2015/0242812 A1 | 8/2015 | Nelson et al. | |

(Continued)

*Primary Examiner* — Bruk A Gebremichael
(74) *Attorney, Agent, or Firm* — Redbrick IP, P.C.

(57) ABSTRACT

The present invention is a system and method to collect and analyze data produced through biometric and psychometric tasks on interactive computing devices. The collected biometric data can be used to quantify motor skills and to generate statistics that correlate with or predict ability in other functional domains. The biometric data tasks and data collection can be incidental to user interaction with a computing device using a touchpad or other input device—such as users drawing lines to connecting screen elements while using the user interface of an application on a computing device.

18 Claims, 8 Drawing Sheets

(56) References Cited

U.S. PATENT DOCUMENTS

2016/0034738 A1 10/2016 Luo
2016/0063236 A1 12/2016 Masuko
2016/0357429 A1 12/2016 Nilo et al.

* cited by examiner

DATA COLLECTION AND ANALYSIS FOR SELF-ADMINISTERED COGNITIVE TESTS CHARACTERIZING FINE MOTOR FUNCTIONS

CROSS-REFERENCE TO RELATED APPLICATION

This application claims priority under 35 U.S.C. § 119(e) to U.S. Provisional Patent Application Ser. No. 62/063,939, "A method and system for the self-administration of biometric data collection for the characterization of fine motor function through interactions with computing devices, particularly touchscreen devices, and the automated generation of summary scores that are predictors of or correlates of the health of associated brain regions or region.", filed Oct. 14, 2014, which is incorporated herein by reference in its entirety.

BACKGROUND

1. Field of the Disclosure

The present invention relates to systems and methods for cognitive testing, and more specifically for a system and method for collecting and analyzing data for characterizing fine motor function.

2. Description of the Related Art

More than 90 million American suffer from a brain disorder that affects their daily functioning. These disorders can be psychological, emotional, motor, cognitive or social in nature. Neuropsychological and neurological testing to identify such disorders is generally performed by a mental health professional to measure a person's cognitive functions, such as memory function, language function, decision making, organization, attention span, reasoning, intellectual capacity, learning or any other brain related functions or disorders as well as motor, social, mood or emotional issues. Traditionally, neuropsychological tests are typically administered in-person by a doctor or skilled clinician, who conducts a variety of physical examinations and tests of motor skills, memory, coordination, reflexes, auditory and visual processing and so forth. Some tests of are administered using a pencil and paper or otherwise manual format. For example, a candidate may be placed in a quiet environment with a clinician and must answer a questionnaire on paper or perform some activity, which is observed and scored by the clinician. Because the tests are scored by a human, there is an unavoidable amount of subjectivity in scoring and ultimate determination of whether the candidate has a deficit.

More specifically, functional assessments using drawing tasks have been paper-based exams on which a user draws with a pen or pencil. Drawing tasks are typically scored by a human observer noting whether or not a line, path, or figure drawn by the user is a valid response to the test item (such as drawing lines to connect matching symbols) and the order and quality of lines drawn. However, the observer's analysis of a user's response in the traditional approach is limited to what the observer can see and many features of the user's response cannot be identified because they occurred below the threshold of human perception.

SUMMARY

One embodiment of the computer-implemented method for conducting self-administered tests comprises configuring a touch-sensitive surface of a client device configured to present a computer-mediated, self-administered test to a user and starting the computer-mediated, self-administrated test. The computer-implemented method receives during the test user inputs on the touch-sensitive surface of a client device and collects motion data in response to the received user inputs. The computer-implemented method generates a trace in response to the test user inputs based on the collected motion data and determines a set of anchor points of the trace. The computer-implemented method further constructs one or more reference paths for the trace based on the set of anchor points and determines a set of diagnostic features of the trace by comparing the trace to the one or more constructed reference paths. A reference path connecting one or more anchor points of the determined set of anchor points.

One embodiment of a non-transitory computer-readable storage medium storing executable computer program instructions for conducting self-administered tests comprises configuring a touch-sensitive surface of a client device configured to present a computer-mediated, self-administered test to a user and starting the computer-mediated, self-administrated test. The non-transitory computer-readable storage medium stores executable computer program instructions for receiving during the test user inputs on the touch-sensitive surface of a client device and collects motion data in response to the received user inputs. The non-transitory computer-readable storage medium stores executable computer program instructions for generating a trace in response to the test user inputs based on the collected motion data and determines a set of anchor points of the trace. The non-transitory computer-readable storage medium stores executable computer program instructions for constructing one or more reference paths for the trace based on the set of anchor points and for determining a set of diagnostic features of the trace by comparing the trace to the one or more constructed reference paths. A reference path connecting one or more anchor points of the determined set of anchor points.

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

BRIEF DESCRIPTION OF THE DRAWINGS

The teachings of the present disclosure can be readily understood by considering the following detailed description in conjunction with the accompanying drawings.

DETAILED DESCRIPTION

Figure 1:
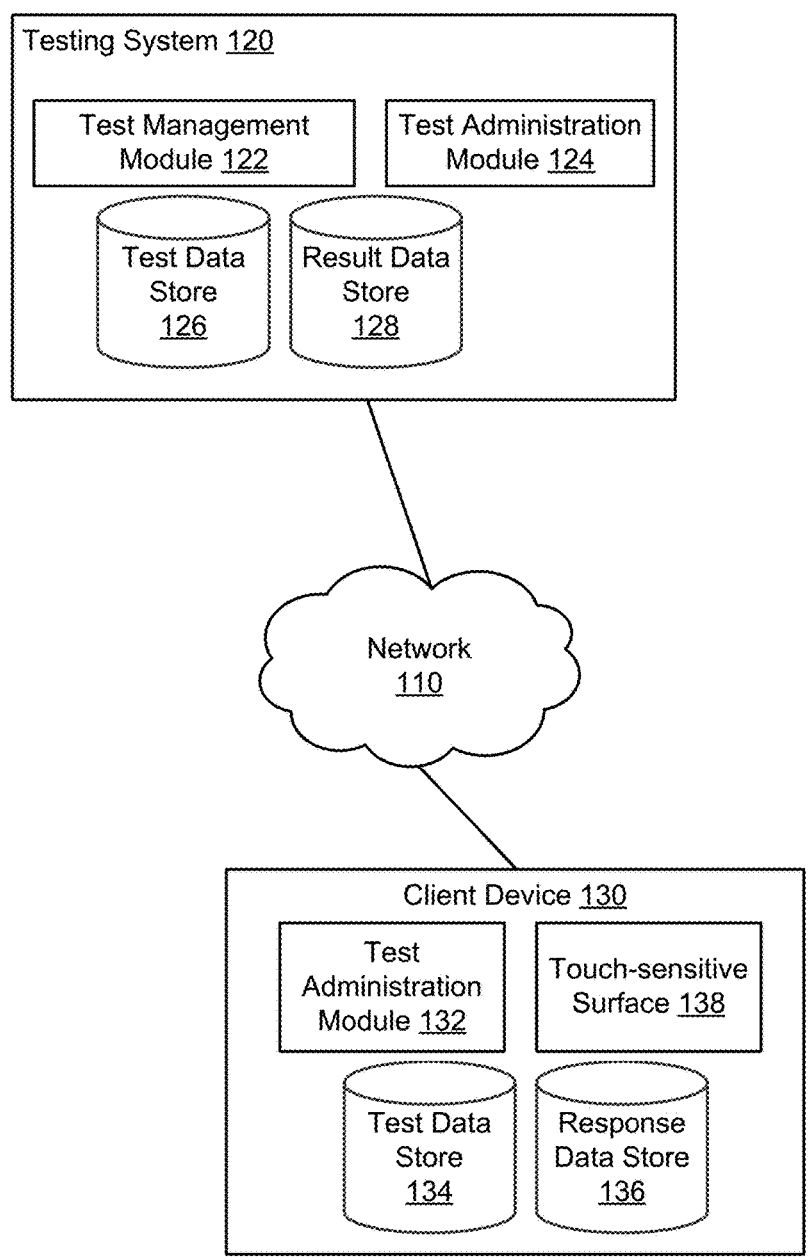
FIG. 1 is a high-level block diagram illustrating an example environment for providing testing, according to one embodiment.

The Figures (FIG.) and the following description relate to various embodiments by way of illustration only. It should be noted that from the following discussion, alternative embodiments of the structures and methods disclosed herein will be readily recognized as viable alternatives that may be employed without departing from the principles discussed herein. Reference will now be made in detail to several embodiments, examples of which are illustrated in the accompanying figures. It is noted that wherever practicable similar or like reference numbers may be used in the figures and may indicate similar or like functionality.

In various embodiments, computer-mediated, task based assessments of neurological disorders include tasks that require the user to draw lines and figures using computer device, coupled to a touch-sensitive surface, such as a touchscreen, for receiving the user's inputs. For example, a test prompts a user to draw lines to connect related words, symbols, or other objects on the touch-sensitive surface, using a designated finger of one of the user's hands. The task may alternatively require the user to connect multiple points or objects to draw a path or figure. The user may also be prompted to draw a figure exactly as it is displayed or to freely draw a path or figure without inclusion of specified anchor points or end-points.

In various embodiments, a client device is configured with a test administration application for conducting computer-mediated self-administered tests for assessing fine motor function. Various embodiments present computer-mediated tasks that collect spatial and temporal information about a user's drawings on a touch-sensitive surface, such as touchscreen of the client device, and determine a user's performance in terms of measurements of motor activity and control. The collected spatial and temporal information may be used to identify deficits in areas of motor, cognitive, social, or emotional functions. Detailed measurement information about a user's drawings or lines, paths, or figures is collected by the client device during assessments of the user's cognitive, motor, emotional, or social capabilities. Self-administered drawing is captured by the device as a sequence of sample points that include values for horizontal position, vertical position, and time. Computationally re-drawing these points in temporal order generates a representation of the user's movement. Representations of user motion are analyzed by the system to generate detailed performance summaries.

The test administration application determines a collection of diagnostic features to quantify fine motor control and other areas of neurological functional performance. The diagnostic features may include features related to line optimality, path velocity, and changes in directions of a user's response. The test application analyzes individual segments between targets (i.e., specified end points for line segments) for tests involving tasks with targets. A target can be a point, a circular region, a symbol, text, a graphical element in a user interface, or regions of other types. Exemplary tasks with targets include matching tasks where a user is required to draw lines to connect related items, or drawing tasks where a user is required to connect a sequence of objects to make a path or figure. The test application may determine anchor points in a user's response when determining diagnostic features. The test application may determine anchor points in a user's response to include target(s) or one or more points within a target. The test application may determine the anchor points to include one or more end points of line segments of a user's response, intersections of lines of a user's response, or points of high curvature of a user's response as anchor points. The test administration application characterizes users' motor, cognitive, psychiatric or other status and performance using detailed summary statistics based on the users' interaction with a computing device.

FIG. 1 is a high-level block diagram illustrating an environment 100 for providing testing, according to one embodiment. As shown, the environment 100 includes a network 110, a testing system 120, and a client device 130. The testing system 120 provides self-administered tests to users over a network 110 via client devices 130. While one testing system 120 and one client device 130 are shown in the example depicted in FIG. 1 for clarity, other embodiments may include different numbers of testing system and client devices. The testing system and its modules are not native components of the underlying computer(s) on which the testing system or client device executes, but rather extend the functionality beyond the generic functions of such computer(s) in the manner described herein.

The network 110 represents the communication pathway between the testing system 120 and the client device 130. In one embodiment, the network 110 uses standard wireless and wired communications technologies and protocols and can include the Internet and associated protocols. In another embodiment, the entities on the network 110 can use custom and/or dedicated data communications technologies. In various embodiments, a communication channel between a client device 130 and a testing system 120 is secured.

The testing system 120 comprises a test management module 122, a test administration module 124, a test data store 126, and a result data store 128. The test management module 122 is configured for creating and managing tests that are designed to assess one or more cognitive capabilities (e.g., intelligence, learning ability, reasoning aptitude, cognitive development, memory, attention etc.), motor skills (e.g., coordination of a certain group of muscle movement, synchronization of hands and fingers, speed), and/or correlations between cognitive, emotional, and motor functions of a user, and is one means for performing these functions. Tests can be tasks that require the users' to respond by completing the tasks using physical inputs to the client device, such as touches, taps, drags, using one or more fingers. A user's input response is measured and analyzed to assess the user's cognitive aptitude, motor skills, and/or correlations between cognitive, emotional, and motor functions in completing the task. For example, a test may involve drawing a trace using finger to connect a series of objects, manipulating graphical representations of objects such as blocks or icons, or memorization of sequences of presented stimuli to test cognitive skills, or a combination thereof. Some tasks may require speech inputs, for example where the user is required to repeat a list of words displayed on a display of the client device 130. The test management module 122 allows an authorized user such as a clinician to create and configure a test such as configuring attributes associated with the test. A test may also include, a set of instructions prompts informing the user how to take the test, required responses, response analysis criteria, and the like. The test data store 126 stores tests and associated attributes.

The test administration module 124 manages, delivers, and conducts self-administered tests, and is one means for performing these functions. A self-administered test includes a series of tasks and is designed to assess one or more cognitive capabilities, motor skills, and/or correlations between cognitive, emotional, and motor functions of a user. The test administration module 124 selects a set of tests stored in the test data store 126 and/or orders the selected tests. The tests may be selected and/or ordered according to a predetermined plan or randomly. The test administration module 124 provides visual or auditory instructions to the user on how to take a self-administered test, presents the tests on the client device via the presentation of graphical objects, images, symbols or the like, then receives the user inputs on the client devices in response to the test. Users' test results including the measurement and analysis of the users' performance are stored in the result data store 128.

A client device 130 is a computing device that includes a touch-sensitive surface 138, such as a touchscreen, or touchpad that enables a user to access the testing system 120 and/or to receive testing service provided by the testing system 120. A client device includes hardware and software modules to provide self-administered tests, to receive user input, and to connect to the network 110 (e.g., via Wi-Fi, Long-Term Evolution (LTE) or other wireless communication protocols). In one example provided throughout the description, the client device 130 is a tablet or smartphone including a touchscreen with operating systems such as ANDROID or APPLE IOS. The touchscreen can be used as both input and output interfaces. The term "module" refers to computer program logic utilized to provide the specified functionality upon execution by the client device 130. Other embodiments of a computing device or a client device 130 can have different and/or other modules than the ones described here, and that the functionalities can be distributed among the modules in a different manner.

The user may access the testing system 120 and/or to receive testing service provided by the testing system 120 in a variety of ways. In some embodiments, a user may download and install a client application of the testing system 120 on the client device 130. Accordingly, as illustrated, in one embodiment, the client device 130 may include a test administration module 132 for delivering and conducting self-administered tests to the user, a test data store 134, and a result data store 136. The test data store 134 may store all or a subset of the tests stored in the test data store 126. The testing system 120 may periodically provide tests to a client device 130. The result data store 136 may store a users' response data such as users' motion data, analysis of users' motion data, users' performance in tests, and the like. The test administration module 132 provides instructions to the user on how to take a self-administered test, monitors, measures, and analyzes the user's performance, and/or returns the user's test result to the user. In some embodiments, the client device 130 provides instructions to the user on how to take a self-administered test, monitors and measures a user's response and provides the user's response to the testing system 120 for analysis, and the testing system 120 returns the user's test result to the client device 130. In some embodiments, a user may access the testing system 120 by logging into the user's account of the testing system 120 using the user's credentials (e.g., using a username/password combination) via the client device 130. The user may take a self-administered test on the testing system 120. A more detailed description of the client device 130 is provided in connection with FIGS. 2 through 11.

Client Device

Figure 2A:
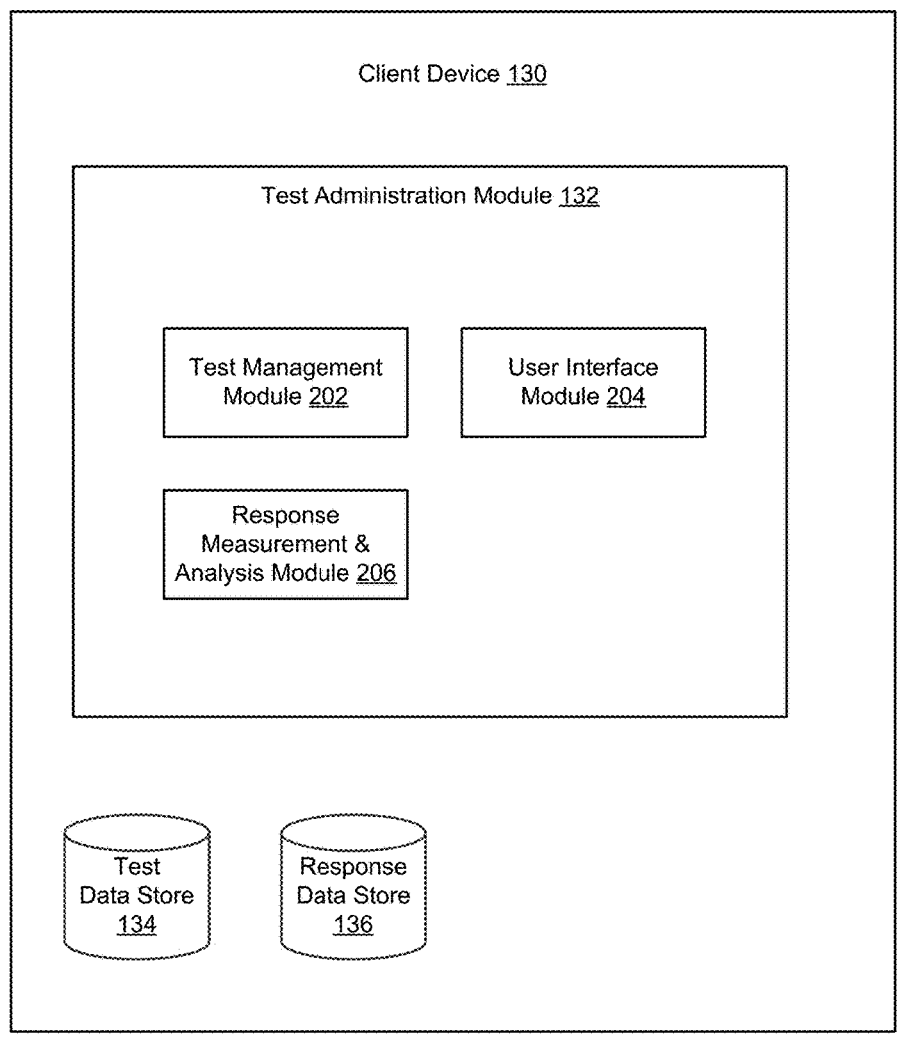
FIG. 2A is a block diagram of an example client device, according to one embodiment.

FIG. 2A is a block diagram of a client device 130, according to one embodiment. The client device 130 comprises a touch-sensitive surface 138, such as a touchscreen, touchpad, or the like, a test administration module 132, a test data store, and a response data store 136. As described in connection with FIG. 1, the test administration module 124 manages, delivers, and conducts self-administered tests. The test administration module 124 allows a user to take a self-administered test. The user provides inputs to the test via a touch-sensitive surface.

The test data store 134 stores various tests that can be taken by a user. Each test stored in the test data store 134 is associated with a set of attributes such as an objective (e.g., to evaluate an cognitive skill, to evaluate an evaluated motor skill, to diagnose a disorder), an instruction (e.g., text, media items such as images, video clips, sound tracks, etc.) to users, a required response (e.g., a particular type of motion, a location of the motion, a timing of the motion, etc.), prohibited motion (e.g., one or more motion restriction regions), measuring of the user's motion (e.g., isolation of motion, etc.), evaluation criteria, etc. The response data store 136 stores the measurement of a user's responses to tests.

The test administration module 132 comprises a test management module 202, a user interface module 204, and a response measurement and analysis module 206. The test management module 202 configures tests for presentation to a user and then administers the tests to the user, and is one means for performing these functions. The test management module 202 may select a set of tests based on the user's test request. The test management module 202 configures the user interface for conducting the test to ensure that instructions associated with a test are accurately presented to the user. The instructions associated with a test provide information to a user to enable the user to understand and respond to the test. For instance, display attributes such as the font, volume, color, and the like of user interface elements are configured to ensure that instructions associated with a test, a test, or a motion restriction region, are displayed to a user. Instructions can be visual or auditory. The test management module 202 may also determine a state of a test and configures the user interface to include a state of the test.

In some embodiments, the test management module 202 may configure the user interface dynamically, for example, based on the user's response. The user's response may be detected by the response measurement and analysis module 206. The test management module 202 may determine various state variables of a test such as a total time of a user taking a test or tests, a current position of a user's finger or cursor in the user interface, whether a task has been completed, or the like. The test management module 202 may configure the user interface to include one or more determined state variables. In some embodiments, the test management module 202 determines whether a user has completed a test. For example, the test management module 202 determines that a user has completed a test when the user has spent greater than a threshold amount of time on taking the test, when the user has responded correctly for a predetermined number of times, when the user has responded incorrectly for a predetermined number of times, or when the user's input is invalid. The test management module 202 may terminate a test when the user has completed the test and configures the user interface to include this information.

The user interface module 204 presents the user interface as configured by the test management module 202 for conducting a test, and is one means for performing these functions. The user interface module 204 presents various user interface elements and instructions associated with the test visually or auditorily to elicit a response from the user (select an answer, connect matching items, or select items in a sequence). For example, the user interface module 204 renders and presents visual objects such as texts or graphics, auditory signals such as speech or music. For example, graphics include text, web pages, icons including user-interface objects including soft keys, digital images, videos, animations, and the like. The user interface module 204 may include computer executable instructions to enable users to respond to a test or test or comply with motion restriction requirement. For example, the user may identify and select regions, portions, locations, or user interface elements presented on the display screen.

The response measurement and analysis module 206 measures and analyzes a user's response to a test, and is one means for performing these functions. The response measurement and analysis module 206 detects a user's motion inputs on the touch-sensitive surface of a client device 130. The touch-sensitive surface 138 of the client device 130 supports multi-touch motions. Different motions have different touch patterns. A touch pattern is characterized by one or more touch points and their associated movements, from which the spatial or geometrical relationships between the touch points can be determined. The response measurement and analysis module 206 may store the touch events captured in the response data store 136. Each touch event is associated with a time, a horizontal position, a vertical position, an event type, a test identifier, and a screen event identifier. In some embodiments, the response measurement and analysis module 206 receives from the underlying operating system motion events including a finger-down event, a finger-up event, and a finger-move event. A finger-down event indicates an initial touch of a position (e.g., a horizontal position and a vertical position) on the touchscreen of the client device 130. A finger-up event indicates the finger is no longer touching the touch screen at substantially the same position as the finger-down event. A finger-move event indicates the finger moves away from the position associated with the finger-down event. A motion event is associated with a time stamp indicating the time of the event.

The response measurement and analysis module 206 evaluates a user's performance in the test using the captured motion events. In various embodiments, a user's response includes a trace (e.g., a path or a figure) drawn by the user on the touch sensitive surface. The response measurement and analysis module 206 may compare the user's response to one or more reference paths (e.g., a linear path, or a smoothed path) to identify diagnostic feature(s) or description(s) of various aspects of the user's behavior and/or performance of the test. The response measurement and analysis module 206 may construct one or more reference paths for analyzing the user's response. In some embodiments, the response measurement and analysis module 206 determines one or more anchor points in the user's response and use the determined anchor points to construct the reference path(s). The response measurement and analysis module 206 may evaluate a user's response in comparison to the reference path(s) to determine diagnostic features related to line optimality, path velocity, or changes in direction of a user's response.

The response measurement and analysis module 206 may analyze the motion data collected during the test to evaluate the user's performance. The test analysis module 208 may analyze a user's responses to multiple tests and determines the user's performance as an aggregation of all the test performances. The response measurement and analysis module 206 may store a user's performance and determined diagnostic features in the response data store 136.

Method of Conducting a Self-Administered Test

Figure 2B:
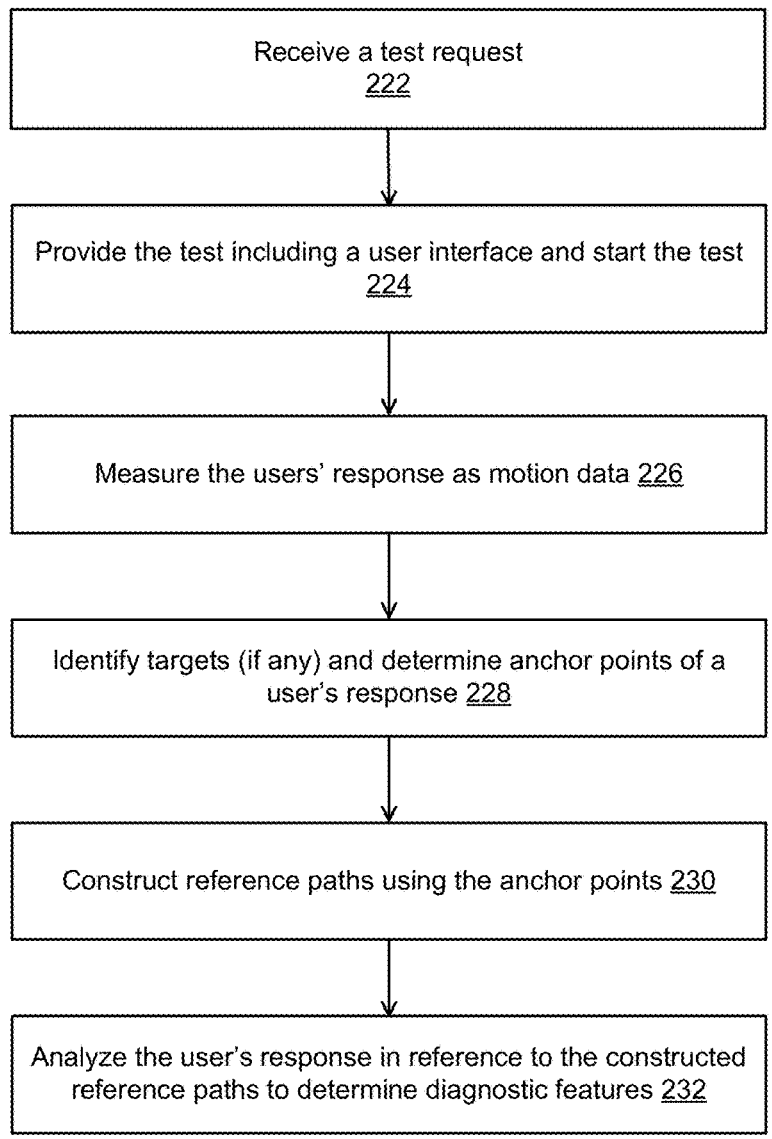
FIG. 2B is a flow diagram of an example method of conducting self-administered tests, according to one embodiment.

FIG. 2B is a flow diagram illustrating an example method 220 of conducting a self-administered test, according to one embodiment. The test administration module 132 receives 222 a test request from a user. A self-administered test includes a series of tasks to assess one or more cognitive capabilities, motor skills, and/or correlations thereof of a user. The test administration module 132 selects 224 tests as requested by the user and. Various tests require a user to draw traces such as paths connecting targets, figures, and the like. A user's response includes continuous or broken lines or curves. The test administration module 132 starts the test. The test administration module configures and provides a user interface of the test to the user and starts the test. The test administration module 132 may configure the user interface for conducting the test to ensure that instructions associated with a test are accurately presented to the user.

The test administration module 132 generates 226 motion data to measure the user's response. In some embodiments, motion data includes motion events as well as time, horizontal locations, vertical locations, event types, test IDs, or screen event IDs associated with the motion events. The motion event types include a finger-down event, a finger-up event, and a finger-move event. A finger-down event indicates an initial touch of a position on the touchscreen of the client device 130. A finger-up event indicates the finger is no longer touching the touch screen at substantially the same position as the finger-down event. A finger-move event indicates the finger moves away from the position associated with the finger-down event. Each motion event corresponds to a point of a user's response that is sampled. The test administration module 132 can characterize a user's response by using the captured motion events.

The test administration module 132 identifies 228 any targets and determines anchor points of a user's response. A target can be a point, a circular region, a symbol, text, a graphical element in a user interface, or regions of other types. For example, the test administration module 132 presents targets such as symbols or graphical elements on the user interface and instructs a user to select, connect, or otherwise interact with. A target can be a point, a circular region, a symbol, text, a graphical element in a user interface, or regions of other types. The test administration module 132 may determine the anchor point(s) to include the centers of the targets. The test administration module 132 may determine the anchor point(s) to include points corresponding to particular positions where the user's response initiates, enters, exits, or terminates within a target. The test administration module 132 may determine various points within a target based on corresponding motion events. For example, a point within a target corresponds to a motion event with the associated location within the target and a final point within a target corresponds to a motion event with the associated time being the latest among all motion events with associated locations within a target. In addition, the test administration module 132 may divide the user's response into multiple line or curve segments and determine the anchor point(s) to include the end points of the line or curve segments. Moreover, the test administration module 132 may determine the anchor point(s) to include breakpoints in a user's response. Furthermore, the test administration module 132 may determine the anchor point(s) to also include: a) a point in the user's response where there is a change in direction (e.g., a region of high curvature), b) a point in the user's response where lines cross (i.e., the user's response intersects itself), and/or c) the points where a user's response crosses predetermined boundaries (e.g., an edge of a graphical element in the user interface).

The test administration module 132 determines a local curvature at each sample point of a user's response and smoothing each local curvature by averaging consecutive local curvatures. The test administration module 132 determines the sample distribution of smoothed local curvatures and identifies the sample points with the smoothed curvatures that are more than twice standard deviations away from the average are changes in direction of a user's response. The test administration module 132 may detect line crossings among all of the straight line segments that interpolate consecutive sample points on a user's response by using the Bentley-Ottmann algorithm or other similar algorithms.

The test administration module constructs 230 one or more reference paths using the determined anchor point(s) by applying various types of curve-fitting models. The test administration module may compare the user's response to reference path(s) to determine diagnostic features or descriptions of various aspects of the user's behavior and/or performance of the test. The reference paths may include a linear path or a smoothed path. The test administration module 132 may construct a linear path as a sequence of line segments connecting the anchor points at the centers of the targets that have been connected by the user. The test administration module 132 may construct a linear path as a sequence of line segments connecting the points at the positions of a first motion event and of a last motion event within each target in the sequence of the user connecting the targets. The test administration module 132 may further construct a linear path as a sequence of line segments connecting all determined anchor points.

The test administration module 132 may determine a smoothed path to include splines (e.g., regression splines) that connect the anchor points at the centers of the targets that have been connected by the user. The test administration module 132 may determine a smoothed path to include splines (e.g., regression splines) that connect a series of points including positions of a first motion event and of a last motion event within each targets (if any) and anchor points in the sequence of the user connecting them. A constructed smoothed path tracks the user's response and also smooths out high frequency "jitters" and sharp changes in directions.

In some embodiments, the test administration module 132 applies cubic splines with a single knot when constructing a smoothed path. The administration module 132 constrains cubic splines and corresponding single knots such that the cubic splines connect the anchor points. In addition, the administration module adjusts the cubic splines and corresponding single knots to reduce a sum of squared residuals between positions of the captured motion events and the smoothed path to be less than a threshold value. The sum of squared residuals between positions of the captured motion events and the smoothed path is in the direction normal to a straight line connecting the anchor points. When the test administration module 132 captures an odd number of motion events, the test administration module 132 includes a single knot with an abscissa at a location on a straight line connecting the anchor points of a projection of the median motion event along the user's response path. When the test administration module 132 captures an even number of motion events, the test administration module 132 determines a location of an abscissa of a single knot at a location on a straight line connecting the anchor points of a projection of the two most medial motion events. The determined smoothed path (e.g., the path 404) tracks the user's response and also smooths out high frequency "jitters" and sharp changes in direction. In further embodiments, the test administration module 132 determines smoother paths such that there are no knots between anchor points or the test administration module 132 applies more flexible models with two or more knots with abscissas evenly spaced along a straight line connecting the anchor points.

The test administration module 132 may apply cubic splines with a single knot to construct a smoothed path. The administration module 132 constrains cubic splines and corresponding single knots such that the cubic splines connect the anchor points. In addition, the administration module optimizes the cubic splines and corresponding single knots to reduce a sum of squared residuals between positions of the captured motion events and the smoothed path to be less than a threshold value. The sum of squared residuals between positions of the captured motion events and the smoothed path is in the direction normal to a straight line connecting the anchor points. When the test administration module 132 captures an odd number of motion events, the test administration module 132 includes a single knot with an abscissa at a location on a straight line connecting the anchor points of a projection of the median motion event along the user's response path. When the test administration module 132 captures an even number of motion events, the test administration module 132 determines a location of an abscissa of a single knot at a location on a straight line connecting the anchor points of a projection of the two most medial motion events. In further embodiments, the test administration module 132 may determine smoother paths, for example, by applying more flexible models with two or more knots with abscissas evenly spaced along a straight line connecting the anchor points.

The test administration module 132 analyzes 232 the user's response to determine diagnostic features. The test administration module 132 may compares the user's response to one or more constructed reference paths to determine the diagnostic features. The test administration module 132 may determine one or more diagnostic features in reference to one or more constructed reference paths such as discrepancies (e.g., difference in length or distance) between a user's response and a constructed linear path, differences (e.g., difference in length or quality of approximation) between a user's response and a constructed smoothed path, distinction between a user's response and a smooth curve, or the like. In addition, the test administration module 132 may identify diagnostic features such as a local speed, a curvature, a maximum speed, a minimum speed, changes in directions, and/or related statistics. Details of determining diagnostic features are described in connection with FIGS. 4 through 6.

Computer Diagram

Figure 3:
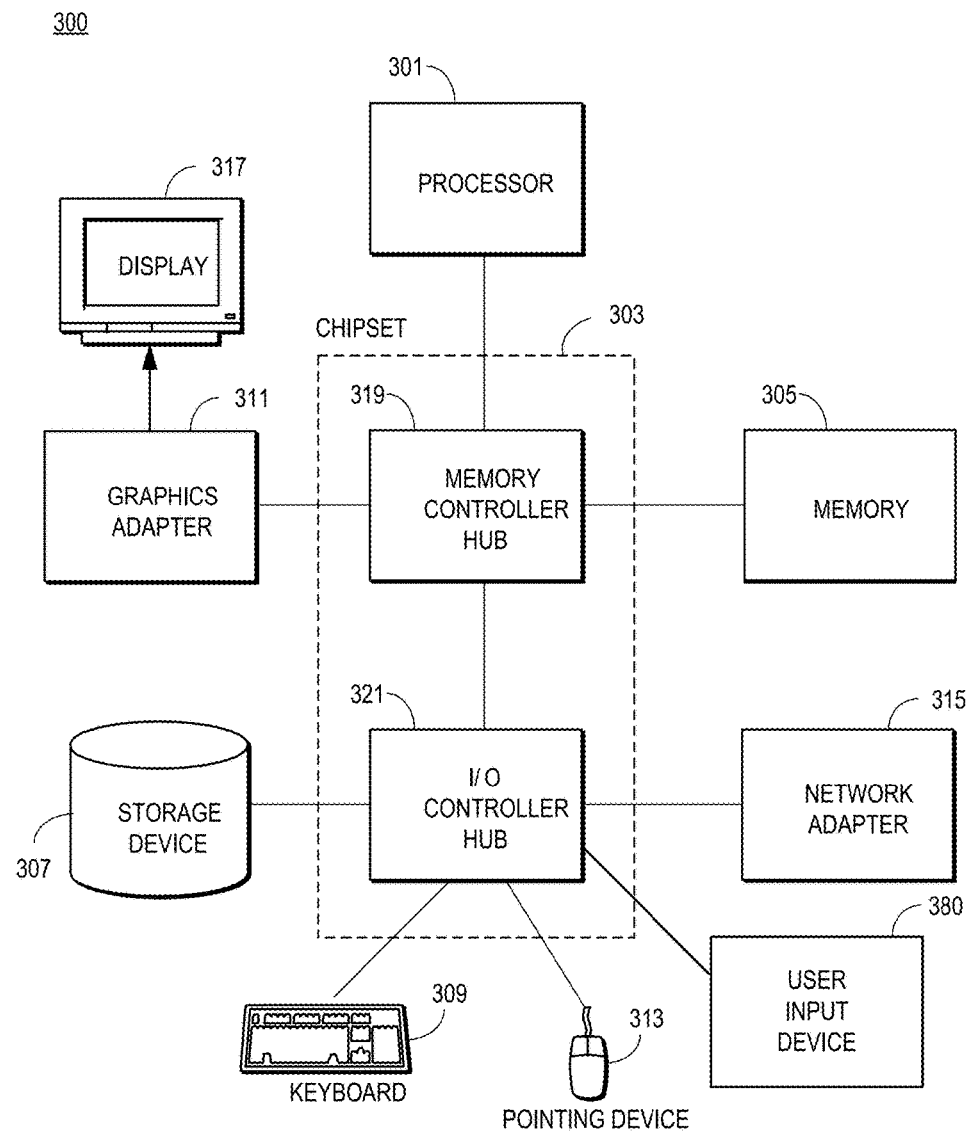
FIG. 3 is a high-level block diagram illustrating a typical computer for acting as a computing device, according to one embodiment.

FIG. 3 is a high-level block diagram of a computer 300 for example, for acting as a computing device according to some embodiments. Illustrated are at least one processor 301 coupled to a chipset 303. Also coupled to the chipset 303 are memory 305, a storage device 307, a keyboard 309, a graphics adapter 311, a pointing device 313, and a network adapter 315, and touch-sensitive surface 380. A display 317 is coupled to the graphics adapter 311. In one embodiment, the functionality of the chipset 303 is provided by a memory controller hub 319 and an I/O controller hub 321. In another embodiment, memory 305 is coupled directly to the processor 301 instead of the chipset 303.

The storage device 307 is any non-transitory computer-readable storage medium, such as a hard drive, compact disk read-only memory (CD-ROM), DVD, or a solid-state memory device. Memory 305 holds instructions and data used by the processor 301. The pointing device 313 may be a mouse, track ball, touch panel, or other type of pointing device, and is used in combination with the keyboard 309 to input data into the computer 300. The touch-sensitive surface 380 is configured to receive touch inputs (including multi-touch inputs). In some embodiments the touch-sensitive surface 380 may be integrated into the display 317, for example in a touchscreen. The graphics adapter 311 displays images and other information on the display 317. The network adapter 315 couples the computer 300 to a local or wide area network (e.g., the network 110 illustrated in FIG. 1).

As is known in the art, a computer 300 can have different and/or other components than those shown in FIG. 2A. In addition, the computer 300 can lack certain illustrated components. As is known in the art, the computer 300 is adapted to execute computer program modules for providing functionality previously described herein. In one embodiment, program modules are stored on the storage device 307, loaded into memory 305, and executed by the processor 301.

Line Optimality Diagnostic Features

Figure 4:
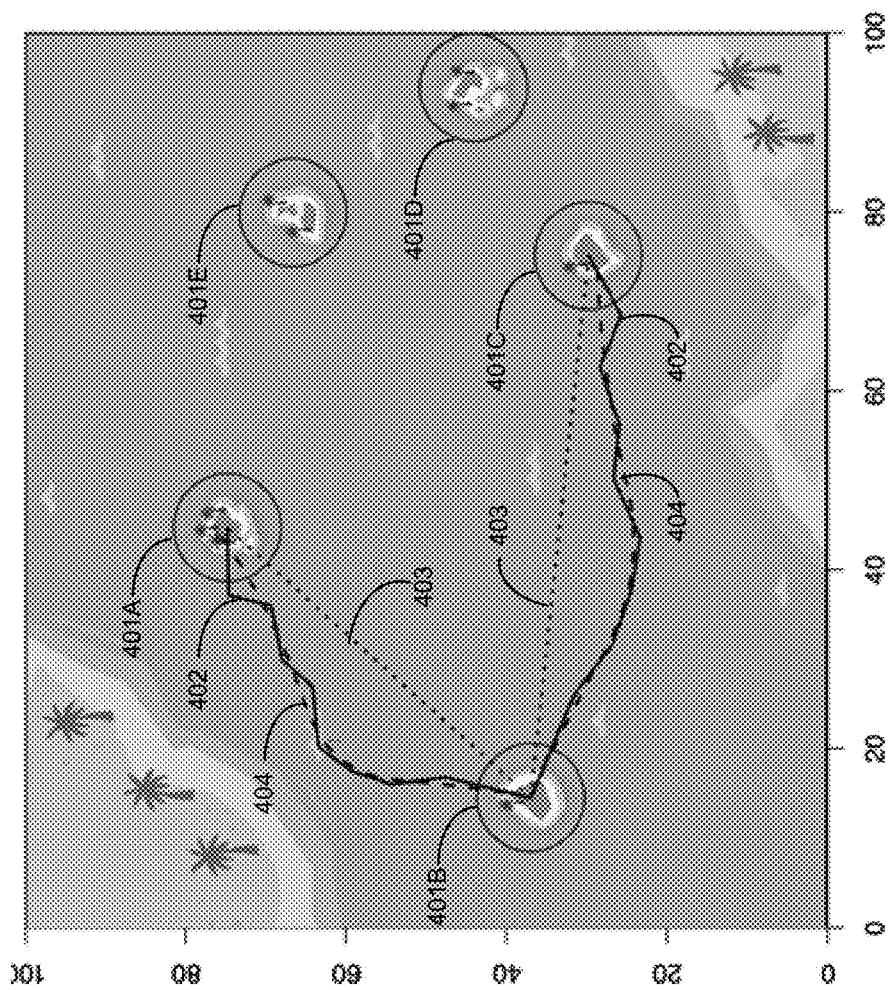
FIG. 4 illustrates an example user interface for conducting self-administered tests, according to one embodiment.

FIG. 4 illustrates an example user interface 400 for conducting self-administered tests, according to one embodiment. In the illustrated example, the self-administered test instructs a user to draw traces to connect islands (i.e., targets 401A-E) without returning to any previously-visited island in one stroke. When a user lifts his or her finger (or other drawing tools), the test administration module 132 terminates the test. As illustrated, a user draws a trace 402 (solid lines) to connect the targets 401A-E (circles). The test administration module 132 collects a user's response data when the user draws the trace 402 on a client device 130. The response data includes a set of motion events associated with event attributes (e.g., time, horizontal position (x), vertical position (y), event type (e.g., finger-down, finger-move, or finger-up)). In various embodiments, the motion events are indexed by time. A user's response data of drawing a trace 402 accordingly includes a finger-down event, followed by a sequence of finger-move events, and finger-up event. As illustrated, the user's response (e.g., the trace 402) is a piecewise linear path that includes a series of segments and connects a series of positions (e.g., (x,y) positions). The test administration module 132 analyzes the user's response data (e.g., a sequence of motion events) to extract summary statistics or numerical biometric features and thereby characterizes the user's performance. In some embodiments, the test administration module 132 may further determine a set of anchor points of a user's response. The test administration module 132 may determine the anchor point(s) to include the centers of the targets. In addition, the test administration module 132 may divide the user's response into multiple line or curve segments and determine the anchor point(s) to include the end points of the line or curve segments. Moreover, the test administration module 132 may determine the anchor point(s) to include breakpoints in a user's response. The test administration module 132 determines the anchor points to also include: a) a point in the user's response where there is a change in direction (e.g., a region of high curvature), b) a point in the user's response where lines cross (i.e., the user's response intersects itself), and/or c) the points where a user's response crosses predetermined boundaries (e.g., an edge of a graphical element in the user interface).

The test administration module 132 constructs one or more reference paths and compares the user's response to the reference paths (e.g., a linear path 403 (dotted line), or a smoothed path 404 (dashed line)) to determine diagnostic features or descriptions of various aspects of the user's behavior and/or performance of the test. In the illustrated example, the test administration module 132 constructs the linear path 403 as a sequence of line segments connecting the anchor points at the centers of the targets that have been connected by the user. The user's response connects the target areas 401A-C and accordingly, the linear path 403 includes segments connecting the centers of the target areas 401A-C and does not connect the target areas 401D-E.

Smoothed paths generalize piecewise linear paths, for example, by connecting anchor points with smooth curves rather than straight lines, which track users' responses more closely. In some embodiments, the test administration module 132 determines a smoothed path to include splines (e.g., regression splines) that connect the anchor points at the centers of the targets that have been connected by the user. In some embodiments, the test administration module 132 determines a smoothed path to include splines (e.g., regression splines) that connect a series of points including positions of a first motion event and of a last motion event within each target areas and anchor points in the sequence of the user connecting them. In some embodiments, the test administration module 132 compares the user's response to one or more references paths (e.g., a linear path 403 (dotted line), or a smoothed path 404 (dashed line)) to determine the diagnostic features including but not limited to:

1) a difference in length between a user's response and a straight line segment between two consecutive anchor points;
2) a sum of squared perpendicular distances from the user's response to the straight line segment between two anchor points;
3) a difference in length between the user's response and a spline fit to the user's response between two anchor points, where the spline is fit to the user's response (e.g., motion events) using a cubic regression spline with one knot placed as described herein; or
4) a sum of squared residuals from the spline fit determined in 3) to the user's response.

The discrepancies between a user's response and a linear path of 1) or 2) may indicate general motor control, planning and attention to the task, drawing style, or physical orientation of the user to a client device. The differences in length of 3) or quality of approximation of the smoothed path and the user's response of 4) may indicate high-frequency jitters in the user's drawings, which can be caused by tremor or Parkinson's disease.

In some cases where a user's response includes two or more contiguously connected segments (e.g., a segment connecting anchor points A and B followed by another segment connecting anchor points B and C), the test administration module 132 determines the following additional diagnostic features:

5) an angle between a first line segment connecting an entry point into a target (the position of the first motion event within the target) to the center of the target, and a second line segment connecting the center of the target and an exit point from the target (the position of the last motion event within the target);
6) an angle between a first line fit to 20 percent of the user's response (e.g., the sample points) between the first and intermediate anchor points (e.g., the anchor points A and B) that are most proximal to the intermediate anchor point, and a second line fit to 20 percent of the user's response (e.g., sample points) between the intermediate and third anchor points (e.g., the anchor points B and C) that are most proximal to the intermediate anchor point;

7) a difference in length between the user's response and a smoothing spline fit to the first, intermediate, and third anchor points.

In further embodiments, the test administration module 132 uses a point with the highest local curvature within the target instead of the center of the target to determine the diagnostic feature of 5). Diagnostic features of 5) and 6) distinguish the user's response from a smooth curve (e.g., a smooth corner at the anchor point B). These features may indicate a user's degree of planning for drawing contiguously connected paths. A production of exaggerated cusps at an intermediate point in a path may show a stylistic signature that can indicate other features. The described analysis and mathematical relationships for determining line optimality diagnostic features are examples of the algorithms implemented by the test administration module 132.

Path Velocity and Curvature Diagnostic Features

Figure 5A:
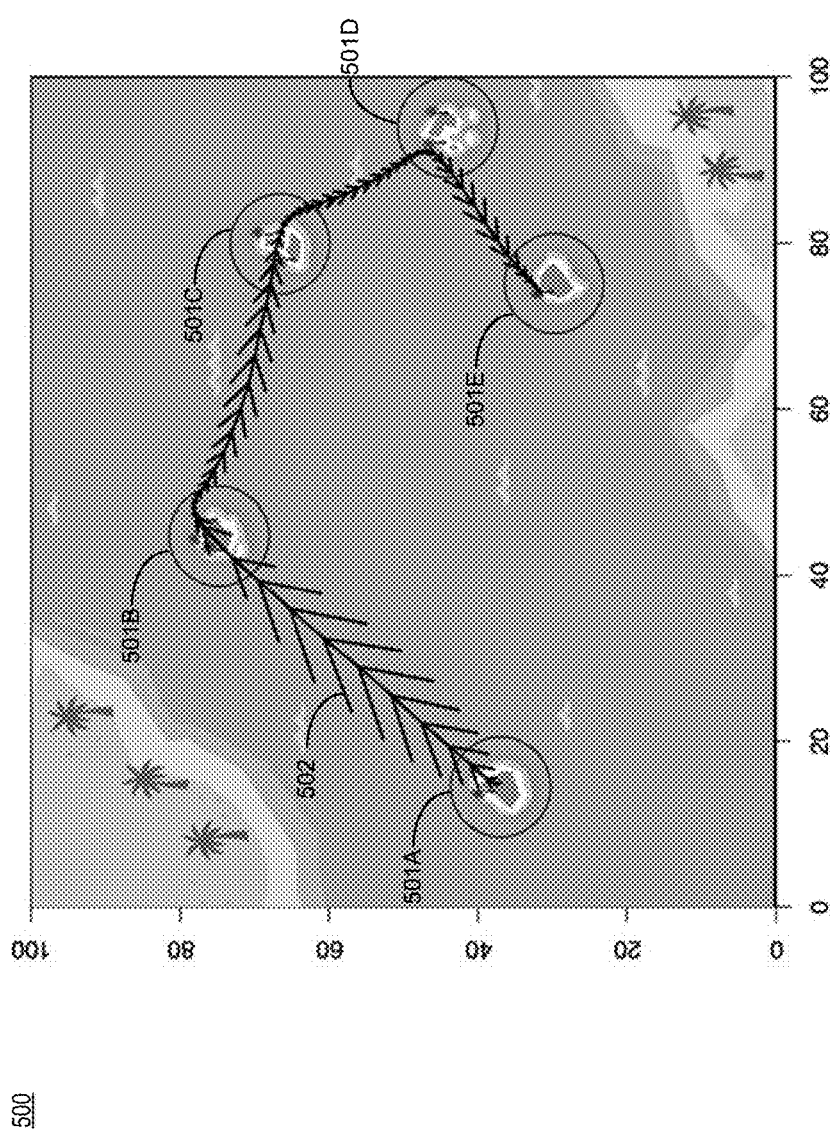
FIG. 5A illustrates an example user interface for conducting self-administered tests, according to one embodiment.
Figure 5B:
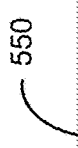
FIG. 5B illustrates an example table of motion events, according to one embodiment.

FIG. 5A illustrates an example user interface 500 for conducting self-administered tests, according to one embodiment. In the illustrated example, the self-administered test instructs a user to draw traces to connect objects (e.g., targets 501A-E). The illustrated arrowheads are proportional to a local speed of the user drawing the response. The test administration module 132 may scale a local speed relative to a maximum speed of the user's response. In the illustrated example, the tips of the arrow heads represent the sample points where the test administration module 132 collects the motion events. In some embodiments, the test administration module 132 of a client device 130 captures motion events and generates a table of motion events including the captured motion events and stores the table in the test data store 134. Referring to FIG. 5B, the illustrated table 550 includes motion events for a test collected by a test administration module 132. Each motion event is associated with a unique test ID 451, a unique screen event ID 452, an event type 453, a time stamp 454, a horizontal position x 455, and a vertical position y 456.

Referring back to FIG. 5A, the test administration module 132 calculates the difference in locations and time between two consecutively-captured motion events thereby to calculate a local speed (i.e., a location difference divided by a time difference) or a curvature of the user's response at a sample point. In some embodiments, the test administration module 132 may identify a maximum speed of the user's response and scale local speeds at sample points relative to the maximum speed. The test administration module 132 may further determine a total length of the user's response. For example, the test administration module 132 determines a length of a segment connecting two consecutive sample points and aggregates the lengths of all segments of a user's response.

The test administration module 132 determines the following diagnostic features:

8) an average speed of the user's response as a total length of the user's response divided by total time of the user's response;

9) a standard deviation of a local speed of a user's response at a sample point that is not an anchor;

10) a maximum or a minimum speed of the user's response;

11) a range of speeds of the user's response;

12) an average curvature of the user's response connecting the targets as an average of determined curvatures of the user's response on all the sample points that are not targets;

13) a standard deviation of a local curvature of a user's response at a sample point that is not an anchor point.

The described analysis and mathematical relationships for determining path velocity and curvature diagnostic features are examples of the algorithms implemented by the test administration module 132.

Changes In Directions Diagnostic Features

Figure 6:
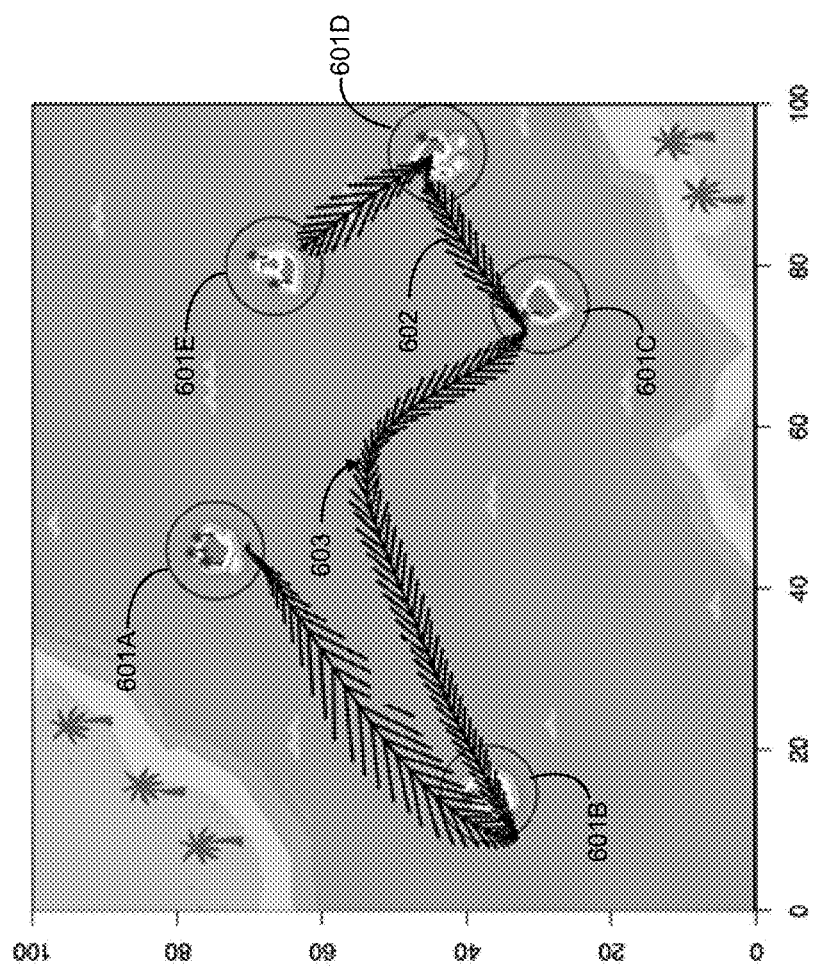
FIG. 6 illustrates an example user interface for conducting self-administered tests, according to one embodiment.

FIG. 6 illustrates an example user interface 600 for conducting self-administered tests, according to one embodiment. In the illustrated example, the self-administered test instructs a user to draw traces to connect objects (e.g., targets 601A-E). The test-administration module 132 may identify sample points or a set of consecutive sample points with local curvatures greater than a curvature threshold, as described herein. The identified sample points or the set of consecutive sample points indicate changes in direction. In addition, the test-administration module 132 may identify the count of changes in direction included in a user's response for a curvature threshold. The count of changes in direction may indicate that the user lacks motor control or decisiveness.

In the illustrated example, the user's response 602 includes a sharp 603 change in direction (or a region of high curvature) of which the curvature is determined to be greater than a curvature threshold. When a user produces multiple drawings that connect the same anchors, for example, by taking the same test repeatedly, the test-administration module 132 may determine multiple sets (or instances) of diagnostic features based on the user's different responses. In further embodiments, the test-administration module 132 may determine additional statistics describing the user's performance using the determined diagnostic features. For example, the test-administration module 132 aggregates multiple instances of a diagnostic feature and calculates statistics (e.g., the mean, median, standard deviation, minimum, or maximum) of the diagnostic feature for the user. The described analysis and mathematical relationships for determining changes in directions diagnostic features are examples of the algorithms implemented by the test administration module 132.

The various algorithms and operations described herein, including the determination of the diagnostic features, is performed by the modules and algorithms described, and in no practical embodiment are they performed by mental steps in the human mind. Upon reading this disclosure, those of skill in the art will appreciate still additional alternative designs for a testing system for providing various self-administered tests. Thus, while particular embodiments and applications of the present disclosure have been illustrated and described, it is to be understood that the embodiments are not limited to the precise construction and components disclosed herein and that various modifications, changes and variations which will be apparent to those skilled in the art may be made in the arrangement, operation and details of the method and apparatus of the present disclosure disclosed herein without departing from the spirit and scope of the disclosure as defined in the appended claims.

What is claimed is:

1. A computer-implemented method for conducting self-administered tests, comprising:
configuring a touch-sensitive surface of a client device configured to present a computer-mediated, self-administered test to a user and starting the computer-mediated, self-administered test;

receiving during the test, user inputs on the touch-sensitive surface of a client device and collecting motion data in response to the received user inputs;

generating a trace in response to the received user inputs based on the collected motion data;

determining a set of anchor points of the trace and constructing one or more reference paths for the trace based on the set of anchor points, a reference path connecting one or more anchor points of the determined set of anchor points; and determining a set of diagnostic features of the trace by comparing the trace to the one or more constructed reference paths, wherein the determining the set of diagnostic features comprises determining a local curvature at the point of the trace, and wherein the determining the set of anchor points comprises comparing the local curvature at the point of the trace to a threshold and determining the point of the trace as an anchor point responsive to determining the local curvature greater than the threshold.

2. The computer-implemented method of claim 1, wherein the computer-mediated, self-administered test is configured to include objects for the user to connect, further comprising identifying one or more targets corresponding to the objects, wherein the set of anchor points comprises centers of the one or more targets.

3. The computer-implemented method of claim 1, wherein the constructing the one or more reference paths comprises constructing a linear path comprising a set of linear line segments connecting one or more anchor points.

4. The computer-implemented method of claim 3, wherein the determining the set of diagnostic features further comprises determining at least one of a difference between a length of the trace and a linear line segment between two anchor points and a sum of squared perpendicular distances from the trace to the linear line segment between the two anchor points.

5. The computer-implemented method of claim 1, wherein the constructing the one or more reference paths comprises constructing a smoothed path comprising a set of splines connecting one or more anchor points.

6. The computer-implemented method of claim 5, wherein the determining the set of diagnostic features further comprises at least determining one of a difference between a length of the trace and a spline between two anchor points and a sum of squared residuals from the spline to the trace.

7. The computer-implemented method of claim 5, wherein the set of splines comprises a cubic spline with a knot and wherein the constructing the reference path comprises constraining the cubic spline and the knot to connect the two anchor points and adjusts the cubic spline and the knot to reduce the sum of squared residuals less than a threshold value.

8. The computer-implemented method of claim 1, wherein the trace includes a first trace segment and a second trace segment, the first trace segment connecting a first anchor point and a second anchor point and the second trace segment connecting the second anchor point and a third anchor point, wherein the determining the set of diagnostic features further comprises determining at least one of a first angle between a first line segment connecting the first and second anchor points and a second line segment connecting the second and third anchor points and a second angle between a third line segment fit to 20 percent of the first trace segment most proximal to the second anchor point and a fourth line segment fit to 20 percent of the second trace segment most proximal to the second anchor point.

9. The computer-implemented method of claim 1, wherein the determining the set of diagnostic features further comprises determining at least one of a local speed at a point of the trace, an average speed of the user, a standard deviation of the local speed at the point of the trace, a maximum speed of the user, a local curvature at the point of the trace, an average curvature of the trace, and a standard deviation of the local curvature.

10. A non-transitory computer-readable storage medium storing executable computer instructions for self-administered tests that, when executed by a hardware processor, perform steps comprising:

configuring a touch-sensitive surface of a client device configured to present a computer-mediated, self-administered test to a user and starting the computer-mediated, self-administered test;

receiving during the test, user inputs on the touch-sensitive surface of a client device and collecting motion data in response to the received user inputs;

generating a trace in response to the received user inputs based on the collected motion data;

determining a set of anchor points of the trace and constructing one or more reference paths for the trace based on the set of anchor points, a reference path connecting one or more anchor points of the determined set of anchor points; and determining a set of diagnostic features of the trace by comparing the trace to the one or more constructed reference paths, wherein the determining the set of diagnostic features comprises determining a local curvature at the point of the trace, and wherein the determining the set of anchor points comprises comparing the local curvature at the point of the trace to a threshold and determining the point of the trace as an anchor point responsive to determining the local curvature greater than the threshold.

11. The non-transitory computer-readable storage medium of claim 10, wherein the computer-mediated, self-administered test is configured to include objects for the user to connect, further comprising instructions configured to cause the processor to perform identifying one or more targets corresponding to the objects, wherein the set of anchor points comprises centers of the one or more targets.

12. The non-transitory computer-readable storage medium of claim 10, wherein the constructing the one or more reference paths comprises constructing a linear path comprising a set of linear line segments connecting one or more anchor points.

13. The non-transitory computer-readable storage medium of claim 12, wherein the determining the set of diagnostic features further comprises determining at least one of a difference between a length of the trace and a linear line segment between two anchor points and a sum of squared perpendicular distances from the trace to the linear line segment between the two anchor points.

14. The non-transitory computer-readable storage medium of claim 10, wherein the constructing the one or more reference paths comprises constructing a smoothed path comprising a set of splines connecting one or more anchor points.

15. The non-transitory computer-readable storage medium of claim 14, wherein the determining the set of diagnostic features further comprises at least determining one of a difference between a length of the trace and a spline between two anchor points and a sum of squared residuals from the spline to the trace.

16. The non-transitory computer-readable storage medium of claim 14, wherein the set of splines comprises a cubic spline with a knot and wherein the constructing the reference path comprises constraining the cubic spline and the knot to connect the two anchor points and adjusts the cubic spline and the knot to reduce the sum of squared residuals less than a threshold value.

17. The non-transitory computer-readable storage medium of claim 10, wherein the trace includes a first trace segment and a second trace segment, the first trace segment connecting a first anchor point and a second anchor point and the second trace segment connecting the second anchor point and a third anchor point, wherein the determining the set of diagnostic features further comprises determining at least one of a first angle between a first line segment connecting the first and second anchor points and a second line segment connecting the second and third anchor points and a second angle between a third line segment fit to 20 percent of the first trace segment most proximal to the second anchor point and a fourth line segment fit to 20 percent of the second trace segment most proximal to the second anchor point.

18. The non-transitory computer-readable storage medium of claim 10, wherein the determining the set of diagnostic features further comprises determining at least one of a local speed at a point of the trace, an average speed of the user, a standard deviation of the local speed at the point of the trace, a maximum speed of the user, a local curvature at the point of the trace, an average curvature of the trace, and a standard deviation of the local curvature.

* * * * *